(12) United States Patent
Muller et al.

(10) Patent No.: US 7,816,393 B2
(45) Date of Patent: *Oct. 19, 2010

(54) ISOINDOLINE COMPOUNDS AND METHODS OF THEIR USE

(75) Inventors: George W. Muller, Bridgewater, NJ (US); Hon-Wah Man, Princeton, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/535,642

(22) Filed: Aug. 4, 2009

(65) Prior Publication Data

US 2009/0291991 A1    Nov. 26, 2009

Related U.S. Application Data

(62) Division of application No. 12/070,322, filed on Feb. 15, 2008, now Pat. No. 7,569,597.

(51) Int. Cl.
*A61K 31/4035* (2006.01)
*C07D 209/48* (2006.01)
*C07D 411/12* (2006.01)

(52) U.S. Cl. ...................................... 514/414; 548/467

(58) Field of Classification Search ................. 548/467; 514/414

See application file for complete search history.

(56) References Cited

U.S. PATENT DOCUMENTS

| | | | |
|---|---|---|---|
| 6,326,388 B1 * | 12/2001 | Man et al. | 514/364 |
| 6,380,239 B1 * | 4/2002 | Muller et al. | 514/417 |
| 7,405,237 B2 * | 7/2008 | Muller et al. | 514/416 |

OTHER PUBLICATIONS

Byrn et al. Solid-State Chemistry of Drugs, 2d, Chapter 11 Hydrates and Solvates, 233-247, 1999.*

* cited by examiner

*Primary Examiner*—Rebecca L Anderson
*Assistant Examiner*—Jason M Nolan

(57) ABSTRACT

Novel isoindoline compounds are disclosed. Methods of treating, preventing and/or managing cancer, diseases and disorders associated with, or characterized by, undesired angiogenesis, and diseases and disorders mediated by PDE 4, using the compounds are also disclosed.

2 Claims, No Drawings

ISOINDOLINE COMPOUNDS AND METHODS OF THEIR USE

CROSS-REFERENCE TO RELATED APPLICATION

This application is a divisional application of U.S. patent application Ser. No. 12/070,322, filed Feb. 15, 2008, now U.S. Pat. No. 7,569,597, which claims the benefit of U.S. patent application Ser. No. 10/900,332, filed Jul. 28, 2004, now U.S. Pat. No. 7,405,237, the disclosures of which are incorporated by reference in their entirety.

1. FIELD OF THE INVENTION

This invention relates to novel isoindoline compounds and their use in methods of treating, preventing and/or managing cancer, and other diseases and disorders including, but not limited to, those associated with, or characterized by, undesired angiogenesis and/or those mediated by PDE 4 inhibition.

2. BACKGROUND OF THE INVENTION

2.1 Pathobiology of Cancer and Other Diseases

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples includes cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, bFGF).

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to: diabetic retinopathy; retinopathy of prematurity; corneal graft rejection; neovascular glaucoma; retrolental fibroplasia; and proliferative vitreoretinopathy.

Accordingly, compounds that can control angiogenesis or inhibit the production of certain cytokines, including TNF-α, may be useful in the treatment and prevention of various diseases and conditions.

2.2 Methods of Treatment

Current cancer therapy may involve surgery, chemotherapy, hormonal therapy and/or radiation treatment to eradicate neoplastic cells in a patient (see, for example, Stockdale, 1998, *Medicine*, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A majority of cancer chemotherapeutics act by inhibiting DNA synthesis, either directly, or indirectly by inhibiting the biosynthesis of deoxyribonucleotide triphosphate precursors, to prevent DNA replication and concomitant cell division. Gilman et al., *Goodman and Gilman's: The Pharmacological Basis of Therapeutics*, Tenth Ed. (McGraw Hill, N.Y.).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove refractory to standard chemotherapeutic treatment protocols.

Other diseases or conditions associated with, or characterized by, undesired angiogenesis are also difficult to treat. However, some compounds such as protamine, hepain and steroids have been proposed to be useful in the treatment of certain specific diseases. Taylor et al., *Nature* 297:307 (1982); Folkman et al., *Science* 221:719 (1983); and U.S. Pat. Nos. 5,001,116 and 4,994,443. Thalidomide and certain derivatives of it have also been proposed for the treatment of such diseases and conditions. U.S. Pat. Nos. 5,593,990, 5,629,327, 5,712,291, 6,071,948 and 6,114,355 to D'Amato. Additional compounds that are reportedly effective are described by U.S. Pat. Nos. 6,380,239 and 6,326,388, both of which are incorporated in their entirety by reference.

Still, there is a significant need for safe and effective methods of treating, preventing and managing cancer and other diseases and conditions, particularly for diseases that are refractory to standard treatments, such as surgery, radiation therapy, chemotherapy and hormonal therapy, while reducing or avoiding the toxicities and/or side effects associated with the conventional therapies.

2.3 PDE 4

Adenosine 3',5'-cyclic monophosphate (cAMP) is another enzyme that plays a role in many diseases and conditions, such as, but not limited to asthma and inflammation (Lowe and Cheng, *Drugs of the Future*, 17(9), 799-807, 1992). The elevation of cAMP in inflammatory leukocytes reportedly inhibits their activation and the subsequent release of inflammatory mediators, including TNF-α and nuclear factor κB (NF-κB). Increased levels of cAMP also lead to the relaxation of airway smooth muscle.

It is believed that primary cellular mechanism for the inactivation of cAMP is the breakdown of cAMP by a family of isoenzymes referred to as cyclic nucleotide phosphodiesterases (PDE) (Beavo and Reitsnyder, *Trends in Pharm.*, 11, 150-155, 1990). There are twelve known members of the family of PDEs. It is recognized that the inhibition of PDE type IV (PDE4) is particularly effective in both the inhibition of inflammatory mediated release and the relaxation of airway smooth muscle (Verghese, et al., *Journal of Pharmacology and Experimental Therapeutics*, 272(3), 1313-1320, 1995). Thus, compounds that specifically inhibit PDE 4 may inhibit inflammation and aid the relaxation of airway smooth muscle with a minimum of unwanted side effects, such as cardiovascular or anti-platelet effects.

The PDE 4 family that is specific for cAMP is currently the largest, and is composed of at least 4 isozymes (a-d), and multiple splice variants (Houslay, M. D. et al. in *Advances in Pharmacology* 44, eds. J. August et al., p. 225, 1998). There may be over 20 PDE 4 isoforms expressed in a cell specific pattern regulated by a number of different promoters. Disease states for which selective PDE4 inhibitors have been sought include: asthma, atopic dermatitis, depression, reperfusion injury, septic shock, toxic shock, endotoxic shock, adult respiratory distress syndrome, autoimmune diabetes, diabetes insipidus, multi-infarct dementia, AIDS, cancer, Crohn's disease, multiple sclerosis, cerebral ischemia, psoriasis, allograft rejection, restenosis, ulceratiave colitis, cachexia, cerebral malaria, allergic rhino-conjunctivitis, osteoarthritis, rheumatoid arthritis, chronic obstructive pulmonary disease (COPD), chronic bronchitis, cosinophilic granuloma, and autoimmune encephalomyelitis (Houslay et al., 1998). PDE 4 is present in the brain and major inflammatory cells and has been found in abnormally elevated levels in a number of diseases including atopic dermatitis or eczema, asthma, and hay fever among others (reference OHSU flyer and *J. of Allergy and Clinical Immunology*, 70: 452-457, 1982 by Grewe et al.). In individuals suffering from atopic diseases elevated PDE 4 activity is found in their peripheral blood mononuclear leukocytes, T cells, mast cells, neutrophils and basophils. This increased PDE activity decreases cAMP levels and results in a breakdown of cAMP control in these cells. This results in increased immune responses in the blood and tissues of those that are affected.

Some PDE 4 inhibitors reportedly have a broad spectrum of anti-inflammatory activity, with impressive activity in models of asthma, chronic obstructive pulmonary disorder (COPD) and other allergic disorders such as atopic dermatitis and hay fever. PDE 4 inhibitors that have been used include theophylline, rolipram, denbufylline, ARIFLO, ROFLUMILAST, CDP 840 (a tri-aryl ethane) and CP80633 (a pyrimidone). PDE 4 inhibitors have been shown to influence eosinophil responses, decrease basophil histamine release, decrease IgE, PGE2, IL10 synthesis, and decrease anti-CD3 stimulated Il-4 production. Similarly, PDE4 inhibitors have been shown to block neutrophil functions. Neutrophils play a major role in asthma, chronic obstructive pulmonary disorder (COPD) and other allergic disorders. PDE 4 inhibitors have been shown to inhibit the release of adhesion molecules, reactive oxygen species, interleukin (IL)-8 and neutrophil elastase, associated with neutrophils which disrupt the architecture of the lung and therefore airway function. PDE 4 inhibitors influence multiple functional pathways, act on multiple immune and inflammatory pathways, and influence synthesis or release of numerous immune mediators. J. M. Hanifin and S. C. Chan, "Atopic Dermatitis-Therapeutic Implication for New Phosphodiesterase Inhibitors," *Monocyte Dysregulation of T Cells in AACI News*, 7/2, 1995; J. M. Hanifin et al., "Type 4 Phosphodiesterase Inhibitors Have clinical and In Vitro Anti-inflammatory Effects in Atopic Dermatitis," *Journal of Investigative Dermatology*, 1996, 107, pp 51-56).

Some of the first generation of PDE 4 inhibitors are effective in inhibiting PDE4 activity and alleviating a number of the inflammatory problems caused by over expression of this enzyme. However, their effectiveness is limited by side effects, particularly when used systemically, such as nausea and vomiting. Huang et al., *Curr. Opin. In Chem. Biol.* 2001, 5:432-438. Indeed, many of the PDE 4 inhibitors developed to date have been small molecule compounds with central nervous system and gastrointestinal side effects, e.g., headache, nausea/emesis, and gastric secretion.

3. SUMMARY OF THE INVENTION

This invention encompasses novel isoindoline compounds and pharmaceutically acceptable salts, solvates, prodrugs, and stereoisomers thereof.

This invention also encompasses methods of treating and preventing cancer. This invention also encompasses methods of treating and preventing certain types of cancer, including primary and metastatic cancer, as well as cancers that are refractory or resistant to conventional chemotherapy. The methods comprise administering to a patient in need of such treatment or prevention a therapeutically or prophylactically effective amount of a compound of this invention, or a pharmaceutically acceptable salt, solvate, stereoisomer, or prodrug thereof.

The invention also encompasses methods of managing cancer (e.g., preventing or prolonging their recurrence, or lengthening the time of remission), which comprise administering to a patient in need of such management a prophylactically effective amount of a compound of this invention, or a pharmaceutically acceptable salt, solvate, hydrate, stereoisomer, clathrate, or prodrug thereof.

In particular methods of the invention, a compound of the invention is administered in combination with a therapy conventionally used to treat, prevent or manage cancer. Examples of such conventional therapies include, but are not limited to, surgery, chemotherapy, radiation therapy, hormonal therapy, biological therapy and immunotherapy.

This invention also encompasses methods of treating, managing and preventing diseases and disorders other than cancer that are associated with, or characterized by, undesired angiogenesis, which comprise administering to a patient in need of such treatment, management or prevention a therapeutically or prophylactically effective amount of a compound of this invention, or a pharmaceutically acceptable salt, solvate, hydrate, stereoisomer, clathrate, or prodrug thereof.

This invention also encompasses methods of treating, managing and preventing diseases and disorders mediated by PDE 4, which comprise administering to a patient in need of such treatment, management or prevention a therapeutically or prophylactically effective amount of a compound of this invention, or a pharmaceutically acceptable salt, solvate, hydrate, stereoisomer, clathrate, or prodrug thereof.

In other methods of the invention, a compound of the invention is administered in combination with a therapy conventionally used to treat, prevent or manage diseases or disorders associated with, or characterized by, undesired angiogenesis or mediated by PDE 4. Examples of such conventional therapies include, but are not limited to, surgery, chemotherapy, radiation therapy, hormonal therapy, biological therapy and immunotherapy.

This invention encompasses pharmaceutical compositions, single unit dosage forms, dosing regimens and kits which comprise a compound of this invention, and optionally a second, or additional, active agent. Second active agents include specific combinations, or "cocktails," of drugs.

4. DETAILED DESCRIPTION OF THE INVENTION

This invention encompasses novel isoindoline compounds described herein, and pharmaceutically acceptable salts, solvates, prodrugs, and stereoisomers thereof.

Another embodiment of the invention encompasses methods of treating, managing, or preventing cancer which comprises administering to a patient in need of such treatment or prevention a therapeutically or prophylactically effective amount of a compound of the invention, or a pharmaceutically acceptable salt, solvate, hydrate, stereoisomer, clathrate, or prodrug thereof.

In particular methods encompassed by this embodiment, a compound of this invention is administered in combination with another pharmacologically active agent ("second active agent") or in conjunction with another method of treating, managing, or preventing cancer. Methods, or therapies, that can be used in combination with the administration of a compound of this invention include, but are not limited to, surgery, blood transfusions, immunotherapy, biological therapy, radiation therapy, and other non-drug based therapies presently used to treat, prevent or manage cancer.

Another embodiment of the invention encompasses methods of treating, managing or preventing diseases and disorders other than cancer that are characterized by undesired angiogenesis. These methods comprise the administration of a therapeutically or prophylactically effective amount of a compound of the invention.

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle). Specific examples of the diseases and disorders associated with, or characterized by, undesired angiogenesis include, but are not limited to, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-syndrome.

Another embodiment of this invention encompasses methods of inhibiting or reducing PDE 4 comprising contacting a compound of this invention with PDE 4. This invention also encompasses methods of inhibiting or reducing the level or activity of PDE 4 in a patient (e.g., human) comprising administering a compound of this invention to the patient. This invention also encompasses methods of treating, managing or preventing diseases and disorders mediated by PDE 4, which comprise the administration of a therapeutically or prophylactically effective amount of a compound of the invention.

Examples of diseases or disorders mediated by PDE 4 include, but are not limited to, asthma, atopic dermatitis, depression, reperfusion injury, septic shock, toxic shock, endotoxic shock, adult respiratory distress syndrome, autoimmune diabetes, diabetes insipidus, multi-infarct dementia, AIDS, cancer, Crohn's disease, multiple sclerosis, cerebral ischemia, psoriasis, allograft rejection, restenosis, ulceratiave colitis, cachexia, cerebral malaria, allergic rhinoconjunctivitis, osteoarthritis, rheumatoid arthritis, chronic obstructive pulmonary disease (COPD), chronic bronchitis, eosinophilic granuloma, and autoimmune encephalomyelitis.

In particular methods encompassed by this embodiment, a compound of the invention is administered in combination with a second active agent, or in addition to other methods of treating, managing, or preventing the disease or condition. Second active agents include small molecules and large molecules (e.g., proteins and antibodies), examples of which are provided herein, as well as stem cells. Methods, or therapies, that can be used in combination with the administration of a compound of this invention include, but are not limited to, surgery, blood transfusions, immunotherapy, biological therapy, radiation therapy, and other non-drug based therapies presently used to treat, prevent or manage disease and conditions associated with, or characterized by, undesired angiogenesis.

The invention also encompasses pharmaceutical compositions (e.g., single unit dosage forms) that can be used in methods disclosed herein. Particular pharmaceutical compositions comprise a compound of the invention and optionally a second active agent.

4.1 Compounds of the Invention

This invention encompasses novel isoindoline compounds, and pharmaceutically acceptable salts, solvates, prodrugs, and stereoisomers thereof, which are described herein.

In one embodiment, this invention encompasses compounds of formula I, and pharmaceutically acceptable salts, solvates, prodrugs, and stereoisomers thereof:

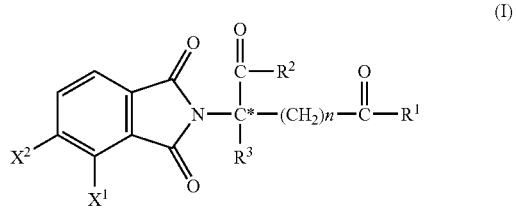

(I)

in which the carbon atom designated C* constitutes a center of chirality (when n is not zero and $R^1$ is not the same as $R^2$); one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if $X^1$ is amino, and n is 1 or 2, then $R^1$ and $R^2$ are not both hydroxy.

In another embodiment, this invention encompasses compounds of formula II, and pharmaceutically acceptable salts, solvates, prodrugs, and stereoisomers thereof:

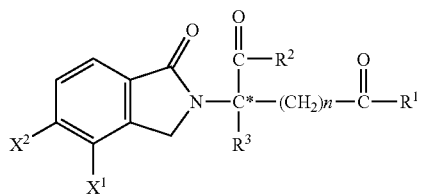

(II)

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl or an alkyl or acyl of one to six carbons; and n has a value of 0, 1, or 2.

Specific examples include, but are not limited to, 2-(4-amino-1-oxo-1,3-dihydro-isoindol-2-yl)-4-carbamoyl-butyric acid and 4-(4-amino-1-oxo-1,3-dihydro-isoindol-2-yl)-4-cabamoyl-butyric acid, which have the following structures, respectively, and pharmaceutically acceptable salts, solvates, prodrugs, and stereoisomers thereof:

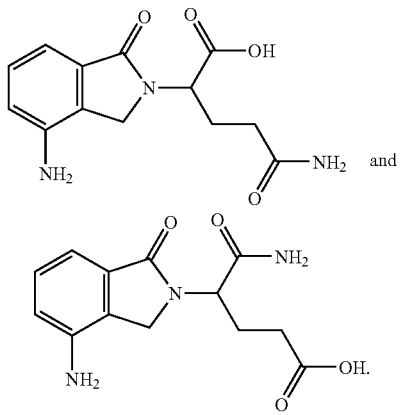

Other representative compounds are of formula:

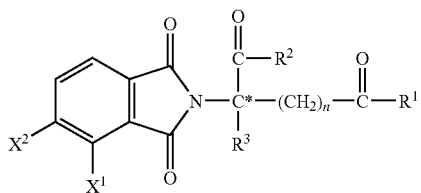

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, an alkyl or acyl of one to six carbons, or furanylalkyl, wherein the alkyl has one to six carbons; and n has a value of 0, 1, or 2; and the pharmaceutically acceptable salts, solvates, prodrugs, and stereoisomers thereof.

Specific examples include, but are not limited to, 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptable salts, solvate, prodrugs, and stereoisomers thereof:

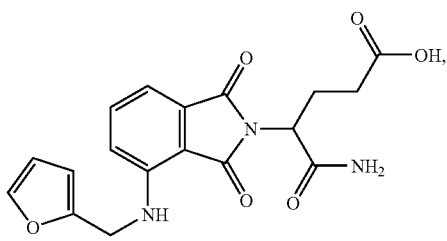

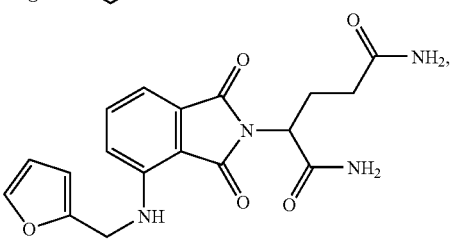

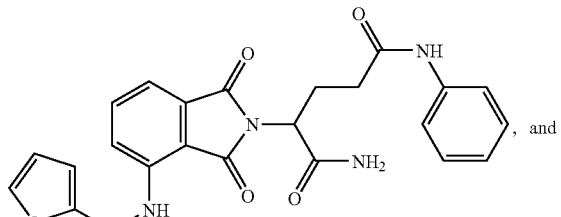

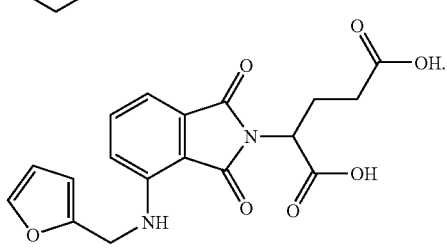

Other specific examples of the compounds are of formula:

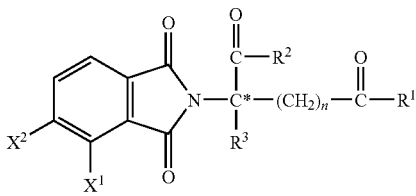

wherein one of $X^1$ and $X^2$ is nitro, or NH-Z, and the other of $X^1$ or $X^2$ is hydrogen;

each of $R^1$ and $R^2$, independent of the other, is hydroxy or NH—Z;

$R^3$ is alkyl of one to six carbons, halo, or hydrogen;

Z is hydrogen, phenyl, an acyl of one to six carbons, or an alkyl of one to six carbons; and n has a value of 0, 1, or 2;

provided that if one of $X^1$ and $X^2$ is nitro, and n is 1 or 2, then $R^1$ and $R^2$ are other than hydroxy; and if —$COR^1$ and —$(CH_2)_n COR^2$ are different, the carbon atom designated C* constitutes a center of chirality. Other representative compounds are of formula:

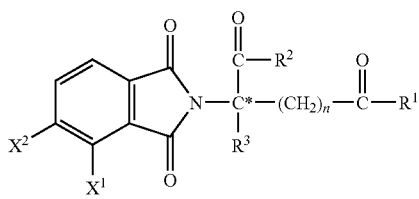

wherein one of $X^1$ and $X^2$ is alkyl of one to six carbons;

each of $R^1$ and $R^2$, independent of the other, is hydroxy or NH—Z;

$R^3$ is alkyl of one to six carbons, halo, or hydrogen;

Z is hydrogen, phenyl, an acyl of one to six carbons, or an alkyl of one to six carbons; and n has a value of 0, 1, or 2; and if —$COR^1$ and —$(CH_2)_n COR^2$ are different, the carbon atom designated C* constitutes a center of chirality.

In another embodiment, this invention encompasses compounds of formula III, and pharmaceutically acceptable salts, solvates, prodrugs, and stereoisomers thereof:

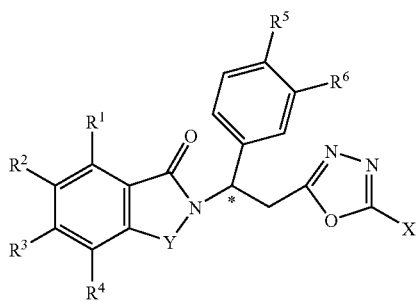

wherein:

the carbon atom designated* constitutes a center of chirality;

Y is C=O, $CH_2$, $SO_2$ or $CH_2C$=O;

X is hydrogen, or alkyl of 1 to 4 carbon atoms;

(i) each of $R^1$, $R^2$, $R^3$, and $R^4$, independently of the others, is hydrogen, halo, trifluoromethyl, acetyl, alkyl of 1 to 8 carbon atoms, alkoxy of 1 to 4 carbon atoms, nitro, cyano, hydroxy, —$CH_2NR^8R^9$, —$(CH_2)_2NR^8R^9$, or —$NR^8R^9$ or (ii) any two of $R^1$, $R^2$, $R^3$, and $R^4$ on adjacent carbon atoms, together with the depicted benzene ring to which they are bound are naphthylidene, quinoline, quinoxaline, benzimidazole, benzodioxole or 2-hydroxybenzimidazole;

each of $R^5$ and $R^6$, independently of the other, is hydrogen, alkyl of 1 to 4 carbon atoms, alkoxy of 1 to 6 carbon atoms, cyano, benzocycloalkoxy, cycloalkoxy of up to 18 carbon atoms, bicyloalkoxy of up to 18 carbon atoms, tricylcoalkoxy of up to 18 carbon atoms, or cycloalkylalkoxy of up to 18 carbon atoms;

(i) each of $R^8$ and $R^9$, independently of the other, is hydrogen, alkyl of 1 to 8 carbon atoms, phenyl, benzyl, pyridyl, pyridylmethyl, or (ii) one of $R^8$ and $R^9$ is hydrogen and the other is —$COR^{10}$, or —$SO_2R^{10}$, in which $R^{10}$ is hydrogen, alkyl of 1 to 8 carbon atoms, cycloalkyl, cycloalkylmethyl of up to 6 carbon atoms, phenyl, pyridyl, benzyl, imidazolylmethyl, pyridylmethyl, $NR^{11}R^{12}$, or $CH_2NR^{14}R^{15}$, wherein $R^{11}$ and $R^{12}$, independently of each other, are hydrogen, alkyl of 1 to 8 carbon atoms, phenyl, or benzyl and $R^{14}$ and $R^{15}$, independently of each other, are hydrogen, methyl, ethyl, or propyl; or (iii) $R^8$ and $R^9$ taken together are tetramethylene, pentamethylene, hexamethylene, —CH=NCH=CH—, or —$CH_2CH_2X^1CH_2CH_2$— in which $X^1$ is —O—, —S—, or —NH—.

Specific examples include, but are not limited to, cyclopropanecarboxylic acid {2-[1-(3-ethoxy-4-methoxy-phenyl)-2-[1,3,4]oxadiazol-2-yl-ethyl]-3-oxo-2,3-dihydro-1H-isoindol-4-yl}-amide, which has the following chemical structure, and pharmaceutically acceptable salts, solvates, prodrugs, and stereoisomers thereof:

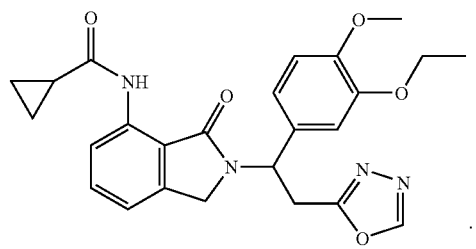

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases known in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

Neutral forms of some compounds may be regenerated by contacting the salt with a base or acid and isolating the parent compound in the conventional manner. The parent form of a compound can differ from its various salt forms in certain physical properties, such as solubility in polar solvents, but the salts are typically equivalent to the parent form of the compound for the purposes of the present invention.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of compounds of this invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of a compound of this invention that comprise —NO, —NO$_2$, —ONO, or —ONO$_2$ moieties. Prodrugs can typically be prepared using well-known methods, such as those described in 1 *Burger's Medicinal Chemistry and Drug Discovery*, 172-178, 949-982 (Manfred E. Wolff ed., 5th ed. 1995), and *Design of Prodrugs* (H. Bundgaard ed., Elsevier, N.Y. 1985).

As used herein and unless otherwise indicated, the terms "biohydrolyzable amide," "biohydrolyzable ester," "biohydrolyzable carbamate," "biohydrolyzable carbonate," "biohydrolyzable ureide," and "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

Various compounds of the invention contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of compounds of this invention may be used in methods and compositions of the invention. The purified (R) or (S) enantiomers of the specific compounds disclosed herein may be used substantially free of its other enantiomer.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound.

As used herein and unless otherwise indicated, the term "enantiomerically pure" means a stereomerically pure composition of a compound having one chiral center. Similarly, the term "enantiomerically enriched" means a stereomerically enriched composition of a compound having one chiral center.

Certain compounds of the present invention can exist in unsolvated forms as well as solvated forms, including hydrated forms. In general, solvated forms are equivalent to unsolvated forms. Certain compounds of the invention may exist in multiple crystalline or amorphous forms. In general, all physical forms are equivalent for the uses contemplated by the present invention, and are encompassed by the present invention.

Certain compounds of the present invention possess asymmetric carbon atoms (optical or stereo-centers) or double bonds; the racemates, enantiomers, diastereomers, geometric isomers and mixtures thereof are all intended to be encompassed by this invention.

Compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic agents, e.g., cancer therapeutic agents, research reagents, e.g., assay reagents, and diagnostic agents, e.g., in vivo imaging agents. All isotopic variations of the compounds of the present invention, whether radioactive or not, are intended to be encompassed within the scope of the present invention.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4.2 Second Active Agents

Compounds of this invention can be combined with other pharmacologically active compounds ("second active agents") in methods and compositions of the invention. It is believed that certain combinations work synergistically in the treatment of particular types of cancer and certain diseases and conditions associated with, or characterized by, undesired angiogenesis. Compounds of this invention can also work to alleviate adverse effects associated with certain second active agents, and some second active agents can be used to alleviate adverse effects that may be associated with compounds of this invention.

One or more second active ingredients or agents can be used in the methods and compositions of the invention together with a compound of the invention. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetylyase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); P13K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies.

Typical large molecule active agents are biological molecules, such as naturally occurring or artificially made proteins. Proteins that are particularly useful in this invention include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions of the invention include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

This invention encompasses the use of native, naturally occurring, and recombinant proteins. The invention further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Large molecule active agents may be administered in the form of anti-cancer vaccines. For example, vaccines that secrete, or cause the secretion of, cytokines such as IL-2, G-CSF, and GM-CSF can be used in the methods, pharmaceutical compositions, and kits of the invention. See, e.g., Emens, L. A., et al., *Curr. Opinion Mol. Ther.* 3(1):77-84 (2001).

In one embodiment of the invention, the large molecule active agent reduces, eliminates, or prevents an adverse effect associated with the administration of a compound of this invention. Depending on the particular compound and the disease or disorder being treated, adverse effects may include, but are not limited to, drowsiness and somnolence, dizziness and orthostatic hypotension, neutropenia, infections that result from neutropenia, increased HIV-viral load, bradycardia, Stevens-Johnson Syndrome and toxic epidermal necrolysis, and seizures (e.g., grand mal convulsions). A specific adverse effect is neutropenia.

Second active agents that are small molecules can also be used to alleviate adverse effects associated with the administration of a compound of this invention. However, like some large molecules, many are believed to be capable of providing a synergistic effect when administered with (e.g., before, after or simultaneously) a compound of the invention. Examples of small molecule second active agents include, but are not limited to, anti-cancer agents, antibiotics, immunosuppressive agents, and steroids.

Examples of anti-cancer agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylispermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist, thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in multiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

4.3 Methods of Treatments and Prevention

Methods of this invention encompass methods of treating, preventing and/or managing various types of cancer, diseases and disorders associated with, or characterized by, undesired angiogenesis, and diseases and disorders mediated by PDE 4, which comprise administering to a patient in need of such treatment, prevention and/or management an effective amount of a compound of this invention. As used herein, unless otherwise specified, the term "treating" refers to the administration of a compound of the invention or other additional active agent after the onset of symptoms of the particular disease or disorder. As used herein, unless otherwise specified, the term "preventing" refers to the administration prior to the onset of symptoms, particularly to patients at risk of cancer, and other diseases and disorders associated with, or characterized by, undesired angiogenesis. The term "prevention" includes the inhibition of a symptom of the particular disease or disorder. Patients with familial history of cancer and diseases and disorders associated with, or characterized by, undesired angiogenesis are preferred candidates for preventive regimens. As used herein and unless otherwise indicated, the term "managing" encompasses preventing the recurrence of the particular disease or disorder in a patient who had suffered from it, and/or lengthening the time a patient who had suffered from the disease or disorder remains in remission.

As used herein, and unless otherwise specified, the term "effective amount" refers to the amount of the compound being administered sufficient to prevent development of or alleviate to some extent one or more of the symptoms of the condition or disorder being treated as well as to alleviate or eradicate the cause of the disease itself.

As used herein, the term "cancer" includes, but is not limited to, solid tumors and blood born tumors. The term "cancer" refers to disease of skin tissues, organs, blood, and vessels, including, but not limited to, cancers of the bladder, bone or blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus. The cancer can be primary or metastatic. Specific cancers include, but are not limited to, advanced malignancy, amyloidosis, neuroblastoma, meningioma, atypical meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, melanoma, including, but not limited to, metastatic melanoma (localized melanoma, including ocular melanoma), malignant mesothelioma, malignant pleural effusion mesothelioma syndrome, peritoneal carcinoma, papillary serous carcinoma, gynecologic sarcoma, soft tissue sarcoma, scelroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, myeloma including, but not limited to, multiple myeloma, smoldering myeloma and indolent myeloma, fallopian tube cancer, androgen independent prostate cancer, androgen dependent stage IV non-metastatic prostate cancer, hormone-insensitive prostate cancer, chemotherapy-insensitive prostate cancer, carcinoma including, but not limited to, papillary thyroid carcinoma, follicular thyroid carcinoma, and medullary thyroid carcinoma, and leiomyoma. In a specific embodiment, the cancer is metastatic. In another embodiment, the cancer is refractory or resistance to chemotherapy or radiation; in particular, refractory to thalidomide.

As used herein, and unless otherwise specified, the terms "diseases or disorders associated with, or characterized by, undesired angiogenesis," "diseases or disorders associated with undesired angiogenesis," and "diseases or disorders characterized by undesired angiogenesis" refer to diseases, disorders and conditions that are caused, mediated or attended by undesired, unwanted or uncontrolled angiogenesis, including, but not limited to, inflammatory diseases, autoimmune diseases, genetic diseases, allergic diseases, bacterial diseases, ocular neovascular diseases, choroidal neovascular diseases, and retina neovascular diseases.

Examples of such diseases or disorders associated with undesired angiogenesis include, but are not limited to, endometriosis, Crohn's disease, heart failure, advanced heart failure, renal impairment, diabetic retinopathy, retinopathy of prematurity, corneal graft rejection, neovascular glaucoma, retrolental fibroplasia, proliferative vitreoretinopathy, trachoma, myopia, optic pits, epidemic keratoconjunctivitis; atopic keratitis, superior limbic keratitis, pterygium keratitis sicca, sjogrens, acne rosacea, phylectenulosis, syphilis, lipid degeneration, bacterial ulcer, fungal ulcer, Herpes simplex infection, Herpes zoster infection, protozoan infection, Kaposi sarcoma, Mooren ulcer, Terrien's marginal degeneration, mariginal keratolysis, myelodysplastic syndrome, rheumatoid arthritis, systemic lupus, polyarteritis, trauma, Wegeners sarcoidosis, scleritis, Steven's Johnson disease, periphigoid radial keratotomy, sickle cell anemia, sarcoid, pseudoxanthoma elasticum, Pagets disease, vein occlusion, artery occlusion, carotid obstructive disease, chronic uveitis, chronic vitritis, Lyme's disease, Eales disease, Bechet's disease, retinitis, choroiditis, presumed ocular histoplasmosis, Bests disease, Stargarts disease, pars planitis, chronic retinal detachment, hyperviscosity syndromes, toxoplasmosis, rubeosis, sarcodisis, sclerosis, soriatis, psoriasis, primary sclerosing cholangitis, proctitis, primary biliary srosis, idiopathic pulmonary fibrosis, alcoholic hepatitis, endotoxemia, toxic shock syndrome, osteoarthritis, retrovirus replication, wasting, meningitis, silica-induced fibrosis, asbestos-induced fibrosis, malignancy-associated hypercalcemia, stroke, circulatory shock, periodontitis, gingivitis, macrocytic anemia, refractory anemia, 5q-syndrome, and veterinary disorder caused by feline immunodeficiency virus, equine infectious anemia virus, caprine arthritis virus, visna virus, maedi virus or lenti virus.

In specific embodiments of the invention, diseases or disorders associated with undesired angiogenesis do not include congestive heart failure, cardiomyopathy, pulmonary edema, endotoxin-mediated septic shock, acute viral myocarditis, cardiac allograft rejection, myocardial infarction, HIV, hepatitis, adult respiratory distress syndrome, bone-resorption disease, chronic obstructive pulmonary diseases, chronic pulmonary inflammatory disease, dermatitis, cystic fibrosis, septic shock, sepsis, endotoxic shock, hemodynamic shock, sepsis syndrome, post ischemic reperfusion injury, fibrotic disease, cachexia, graft rejection, rheumatoid spondylitis, osteoporosis, ulcerative colitis, inflammatory-bowel disease, multiple sclerosis, systemic lupus erythrematosus, erythema nodosum leprosum in leprosy, radiation damage, asthma, hyperoxic alveolar injury, malaria, mycobacterial infection, and opportunistic infections resulting from HIV.

As used herein, and unless otherwise specified, the term "diseases or disorders mediated by PDE 4" means a condition or disorder that responds favorably to modulation, for example, reduction (e.g., inhibition), of PDE 4 activity. Favorable responses to PDE 4 modulation include alleviation or abrogation of the disease and/or its attendant symptoms, inhibition of the disease (i.e., arrest or reduction of the development of the disease), or its clinical symptoms, and regression of the disease or its clinical symptoms. A disease or disorder mediated by PDE 4 may be completely or partially responsive to PDE 4 modulation. A disease or disorder mediated by PDE 4 may be associated with inappropriate, e.g., less than or greater than normal, PDE 4 activity. Inappropriate PDE 4 functional activity might arise as the result of PDE 4 expression in cells which normally do not express PDE 4, decreased PDE 4 expression (leading to, e.g., lipid and metabolic disorders and diseases) or increased PDE 4 expression.

As used herein, and unless otherwise specified, the terms "modulate" and "modulation" means that the activity or expression of the molecule (e.g., an enzyme) to be modulated is enhanced or decreased. In some embodiments, the activity or expression of the molecule to be modulated is enhanced by 10%, 20%, 50%, 100%, or 200% or more, as compared to the activity or expression of the molecule without the modulation. In other embodiments, the activity or expression of the molecule to be modulated is decreased by 10%, 20%, 50%, 70%, 80%, or 90% or more, as compared to the activity or expression of the molecule without the modulation.

Examples of diseases or disorders mediated by PDE 4 include, but are not limited to, asthma, atopic dermatitis, depression, reperfusion injury, septic shock, toxic shock, endotoxic shock, adult respiratory distress syndrome, autoimmune diabetes, diabetes insipidus, multi-infarct dementia, AIDS, cancer, Crohn's disease, multiple sclerosis, cerebral ischemia, psoriasis, allograft rejection, restenosis, ulceratiave colitis, cachexia, cerebral malaria, allergic rhinoconjunctivitis, osteoarthritis, rheumatoid arthritis, chronic obstructive pulmonary disease (COPD), chronic bronchitis, cosinophilic granuloma, and autoimmune encephalomyelitis.

This invention encompasses methods of treating patients who have been previously treated for cancer, diseases or disorders associated with, or characterized by, undesired angiogenesis, or diseases or disorders mediated by PDE 4, but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer and diseases and disorders characterized by undesired angiogenesis or mediated by PDE 4 have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer and other diseases or disorders.

Methods encompassed by this invention comprise administering one or more compounds of the invention to a patient (e.g., a human) who is suffering, or likely to suffer, from cancer, a disease or disorder mediated by undesired angiogenesis, or a disease or disorder mediated by PDE 4.

In one embodiment of the invention, the recommended daily dose range of a compound of this invention for the conditions described herein lie within the range of from about 1 mg to about 10,000 mg per day, given as a single once-a-day dose, or preferably in divided doses throughout a day. More specifically, the daily dose is administered twice daily in equally divided doses. Specifically, a daily dose range should be from about 1 mg to about 5,000 mg per day, more specifically, between about 10 mg and about 2,500 mg per day, between about 100 mg and about 800 mg per day, between about 100 mg and about 1,200 mg per day, or between about 25 mg and about 2,500 mg per day. In managing the patient, the therapy should be initiated at a lower dose, perhaps about 1 mg to about 2,500 mg, and increased if necessary up to about 200 mg to about 5,000 mg per day as either a single dose or divided doses, depending on the patient's global response.

4.3.1 Combination Therapy with a Second Active Agent

Specific methods of the invention comprise administering a compound of this invention, or a pharmaceutically acceptable salt, solvate, hydrate, stereoisomer, clathrate, or prodrug thereof, in combination with one or more second active agents, and/or in combination with radiation therapy, blood transfusions, or surgery. Examples of second active agents are also disclosed herein (see, e.g., section 4.2).

Administration of the compound of this invention and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for a compound of this invention of the invention is oral or ophthalmic. Preferred routes of administration for the second active agents or ingredients of the invention are known to those of ordinary skill in the art. See, e.g., *Physicians'Desk Reference,* 1755-1760 ($56^{th}$ ed., 2002).

In one embodiment of the invention, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds of the invention and any optional additional active agents concurrently administered to the patient. In a particular embodiment, the second active agent is oblimersen (Genasense®), GM-CSF, G-CSF, EPO, taxotere, irinotecan, dacarbazine, transretinoic acid, topotecan, pentoxifylline, ciprofloxacin, dexamethasone, vincristine, doxorubicin, cox-2 inhibitors, IL2, IL8, IL18, IFN, Ara-C, vinorelbine, or a combination thereof.

In a particular embodiment, GM-CSF, G-CSF or EPO is administered subcutaneously during about five days in a four or six week cycle in an amount of from about 1 to about 750 mg/m$^2$/day, preferably in an amount of from about 25 to about 500 mg/m$^2$/day, more preferably in an amount of from about 50 to about 250 mg/m$^2$/day, and most preferably in an amount of from about 50 to about 200 mg/m$^2$/day. In a certain embodiment, GM-CSF may be administered in an amount of from about 60 to about 500 mcg/m$^2$ intravenously over 2 hours, or from about 5 to about 12 mcg/m$^2$/day subcutaneously. In a specific embodiment, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In a certain embodiment, EPO may be administered subcutaneously in an amount of 10,000 Unit 3 times per week.

In another embodiment, a compound of this invention is administered in an amount of from about 20 mg to about 1,200 mg/d alone or in combination with a second active agent to patients with metastatic melanoma (localized melanoma, including, but not limited to, ocular melanoma). In one embodiment, a compound of this invention in an amount of from about 800 to about 1,200 mg/d and dacarbazine (DTIC) in an amount of from about 200 to about 1000 mg/m$^2$/d are administered to patients with metastatic melanoma (localized melanoma, including, but not limited to, ocular melanoma). In another embodiment, a compound of this invention in an amount of about from 800 to 1,200 mg/d and temozolomide are administered to patients with metastatic melanoma (localized melanoma, including, but not limited to, ocular-melanoma). In another embodiment, a compound of this invention is administered to patients with metastatic melanoma or localized melanoma whose disease has progressed on treatment with temozolomide, dacarbazine (DTIC), IL-2 and/or IFN. In a specific embodiment, a compound of this invention is administered to patients with relapsed or refractory multiple myeloma in combination with dexamethasone.

In another embodiment, a compound of this invention is administered with melphalan and dexamethasone to patients with amyloidosis. In a specific embodiment, a compound of the invention and steroids can be administered to patients with amyloidosis.

In another embodiment, a compound of this invention is administered with gemcitabine and cisplatinum to patients with locally advanced or metastatic transitional cell bladder cancer.

In another embodiment, a compound of this invention is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapased brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In another embodiment, a compound of this invention is administered with methotrexate and cyclophosphamide to patients with metastatic breast cancer.

In another embodiment, a compound of this invention is administered with temozolomide to patients with neuroendocrine tumors.

In another embodiment, a compound of this invention is administered with gemcitabine to patients with recurrent or metastatic head or neck cancer. In another embodiment, a compound of this invention is administered with gemcitabine to patients with pancreatic cancer.

In another embodiment, a compound of this invention is administered to patients with colon cancer in combination with Arisa®, taxol and/or taxotere.

In another embodiment, a compound of this invention is administered with capecitabine to patients with refractory colorectal cancer or patients who fail first line therapy or have poor performance in colon or rectal adenocarcinoma.

In another embodiment, a compound of this invention is administered in combination with fluorouracil, leucovorin, and irinotecan to patients with Dukes C & D colorectal cancer or to patients who have been previously treated for metastatic colorectal cancer.

In another embodiment, a compound of this invention is administered to patients with refractory colorectal cancer in combination with capecitabine, xeloda, and/or CPT-11.

In another embodiment, a compound of the invention is administered with capecitabine and irinotecan to patients with refractory colorectal cancer or to patients with unresectable or metastatic colorectal carcinoma.

In another embodiment, a compound of this invention is administered alone or in combination with interferon alpha or capecitabine to patients with unresectable or metastatic hepatocellular carcinoma; or with cisplatin and thiotepa to patients with primary or metastatic liver cancer.

In another embodiment, a compound of this invention is administered in combination with pegylated interferon alpha to patients with Kaposi's sarcoma.

In another embodiment, a compound of this invention is administered in combination with fludarabine, carboplatin, and/or topotecan to patients with refractory or relapsed or high-risk acuted myelogenous leukemia.

In another embodiment, a compound of this invention is administered in combination with liposomal daunorubicin, topotecan and/or cytarabine to patients with unfavorable karotype acute myeloblastic leukemia.

In another embodiment, a compound of this invention is administered in combination with gemcitabine and irinotecan to patients with non-small cell lung cancer. In one embodiment, a compound of this invention is administered in combination with carboplatin and irinotecan to patients with non-small cell lung cancer. In one embodiment, a compound of this invention is administered with doxetaxol to patients with non-small cell lung cancer who have been previously treated with carbo/VP 16 and radiotherapy.

In another embodiment, a compound of this invention is administered in combination with carboplatin and/or taxotere, or in combination with carboplatin, paclitaxel and/or thoracic radiotherapy to patients with non-small cell lung cancer. In a specific embodiment, a compound of this invention is administered in combination with taxotere to patients with stage IIIB or IV non-small cell lung cancer.

In another embodiment, a compound of this invention is administered in combination with oblimersen (Genasense®) to patients with small cell lung cancer.

In another embodiment, a compound of this invention is administered alone or in combination with a second active ingredient such as vinblastine or fludarabine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In another embodiment, a compound of this invention is administered in combination with taxotere, IL-2, IFN, GM-CSF, and/or dacarbazine to patients with various types or stages of melanoma including, but not limited to, localized melanoma or metastatic melanoma such as ocular melanoma.

In another embodiment, a compound of this invention is administered alone or in combination with vinorelbine to patients with malignant mesothelioma, or stage IIIB non-small cell lung cancer with pleural implants or malignant pleural effusion mesothelioma syndrome.

In another embodiment, a compound of this invention is administered to patients with various types or stages of multiple myeloma in combination with dexamethasone, zoledronic acid, palmitronate, GM-CSF, biaxin, vinblastine, melphalan, busulphan, cyclophosphamide, IFN, palmidronate, prednisone, bisphosphonate, celecoxib, arsenic trioxide, PEG INTRON-A, vincristine, doxil, decadron, or a combination thereof.

In another embodiment, a compound of this invention is administered to patients with relapsed or refractory multiple myeloma in combination with doxorubicin (Doxil®), vincristine and/or dexamethasone (Decadron®).

In another embodiment, a compound of this invention is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, or a combination thereof.

In another embodiment, a compound of this invention is administered to patients with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, or a combination thereof.

In another embodiment, a compound of this invention is administered to patients with various types or stages of renal cell cancer, in combination with capecitabine, IFN, tamoxifen, IL-2, GM-CSF, Celebrex®, or a combination thereof.

In another embodiment, a compound of this invention is administered to patients with various types or stages of gynecologic, uterus or soft tissue sarcoma cancer in combination with IFN, a COX-2 inhibitor such as Celebrex®, and/or sulindac.

In another embodiment, a compound of this invention is administered to patients with various types or stages of solid tumors in combination with celebrex, etoposide, cyclophosphamide, docetaxel, apecitabine, IFN, tamoxifen, IL-2, GM-CSF, or a combination thereof.

In another embodiment, a compound of this invention is administered to patients with scelroderma or cutaneous vasculitis in combination with celebrex, etoposide, cyclophosphamide, docetaxel, apecitabine, IFN, tamoxifen, IL-2, GM-CSF, or a combination thereof.

This invention also encompasses a method of increasing the dosage of an anti-cancer drug or agent that can be safely and effectively administered to a patient, which comprises administering to a patient (e.g., a human) a compound of this invention. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a compound of this invention alleviates or reduces adverse effects which are of such severity that it would otherwise limit the amount of anti-cancer drug.

In one embodiment, a compound of this invention can be administered orally and daily in an amount of from about 1 to about 5,000 mg, from about 10 to about 2,500 mg, from about 25 to about 2,500 mg, from about 100 to about 1,200 mg, or from about 100 to about 800 mg prior to, during, or after the occurrence of the adverse effect associated with the administration of an anti-cancer drug to a patient. In a particular embodiment, a compound of this invention is administered in combination with specific agents such as heparin, aspirin, coumadin, or G-CSF to avoid adverse effects that are associated with anti-cancer drugs such as but not limited to neutropenia or thrombocytopenia.

In one embodiment, a compound of this invention can be administered to patients with diseases and disorders associated with, or characterized by, undesired angiogenesis, optionally in combination with additional active ingredients including but not limited to anti-cancer drugs, anti-inflammatories, antihistamines, antibiotics, and steroids.

In another embodiment, this invention encompasses a method of treating, preventing and/or managing cancer, which comprises administering a compound of this invention, optionally in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compounds of this invention and conventional therapy may provide a unique treatment regimen that is unexpectedly effective in certain patients. Without being limited by theory, it is believed that compound of this invention may provide additive or synergistic effects when given concurrently with conventional therapy.

In another embodiment, this invention encompasses a method of treating, preventing and/or managing diseases and disorders associated with, or characterized by, undesired angiogenesis, which comprises administering a compound of this invention, optionally in conjunction with (e.g. before, during, or after) conventional therapy including, but not limited to, surgery, immunotherapy, biological therapy, radiation therapy, or other non-drug based therapy presently used to treat, prevent or manage diseases and disorders associated with, or characterized by, undesired angiogenesis. The combined use of the compounds of this invention and conventional therapy may provide a unique treatment regimen that is unexpectedly effective in certain patients. Without being limited by theory, it is believed that the compounds of this invention may provide additive or synergistic effects when given concurrently with conventional therapy.

As discussed elsewhere herein, the invention encompasses a method of reducing, treating and/or preventing adverse or undesired effects associated with conventional therapy including, but not limited to, surgery, chemotherapy, radiation therapy, hormonal therapy, biological therapy and immunotherapy. One or more compounds of this invention, optionally with other active ingredient, can be administered to a patient prior to, during, or after the occurrence of the adverse effect associated with conventional therapy.

In one embodiment, a compound of this invention can be administered in an amount of from about 1 to about 5,000 mg, from about 10 to about 2,500 mg, from about 25 to about 2,500 mg, from about 100 to about 1,200 mg, or from about 100 to about 800 mg orally and daily alone, or in combination with a second active agent disclosed herein (see, e.g., section 4.2), prior to, during, or after the use of conventional therapy.

In a specific embodiment of this method, a compound of this invention and doxetaxol are administered to patients with non-small cell lung cancer who were previously treated with carbo/VP 16 and radiotherapy.

4.3.2 Use with Transplantation Therapy

Compounds of the invention can be used to reduce the risk of Graft Versus Host Disease (GVHD). Therefore, the invention encompasses a method of treating, preventing and/or managing cancer, which comprises administering a compound of this invention, optionally in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of the compound of this invention and transplantation therapy provides a unique and unexpected synergism. In particular, a compound of this invention exhibits activity that may provide additive or synergistic effects when given concurrently with transplantation therapy in patients with cancer.

A compound of this invention can work in combination with transplantation therapy reducing complications associated with the invasive procedure of transplantation and risk of GVHD. This invention encompasses a method of treating, preventing and/or managing cancer which comprises administering to a patient (e.g., a human) a compound of this invention, before, during, or after the transplantation of umbilical cord blood, placental blood, peripheral blood stem cell, hematopoietic stem cell preparation or bone marrow. Examples of stem cells suitable for use in the methods of the invention are disclosed in U.S. patent application Ser. No. 10/411,655, filed Apr. 11, 2003 by R. Hariri et al., the entirety of which is incorporated herein by reference.

In another embodiment, this invention encompasses a method of treating, preventing and/or managing diseases and disorders associated with, or characterized by, undesired angiogenesis, which comprises administering to a patient (e.g., a human) a compound of this invention, before, during, or after the transplantation of umbilical cord blood, placental blood, peripheral blood stem cell, hematopoietic stem cell preparation or bone marrow.

In one embodiment of this method, a compound of this invention is administered to patients with multiple myeloma before, during, or after the transplantation of autologous peripheral blood progenitor cell.

In another embodiment, a compound of this invention is administered to patients with relapsing multiple myeloma after the stem cell transplantation.

In another embodiment, a compound of this invention and prednisone are administered as maintenance therapy to patients with multiple myeloma following the transplantation of autologous stem cell.

In another embodiment, a compound of this invention and dexamethasone are administered as salvage therapy for low risk post transplantation to patients with multiple myeloma.

In another embodiment, a compound of this invention and dexamethasone are administered as maintenance therapy to patients with multiple myeloma following the transplantation of autologous bone marrow.

In another embodiment, a compound of this invention is administered following the administration of high dose of melphalan and the transplantation of autologous stem cell to patients with chemotherapy responsive multiple myeloma.

In another embodiment, a compound of this invention and PEG INTRO-A are administered as maintenance therapy to patients with multiple myeloma following the transplantation of autologous CD34-selected peripheral stem cell.

In another embodiment, a compound of this invention is administered with post transplant consolidation chemotherapy to patients with newly diagnosed multiple myeloma to evaluate anti-angiogenesis.

In another embodiment, a compound of this invention and dexamethasone are administered as maintenance therapy after DCEP consolidation, following the treatment with high dose of melphalan and the transplantation of peripheral blood stem cell to 65 years of age or older patients with multiple myeloma.

4.3.3 Cycling Therapy

In certain embodiments, the prophylactic or therapeutic agents of the invention are cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one specific embodiment of the invention, a compound of this invention is administered daily in a single or divided doses in a four to six week cycle with a rest period of about a week or two weeks. The invention further allows the frequency, number, and length of dosing cycles to be increased. Thus, another specific embodiment of the invention encompasses the administration of a compound of this invention for more cycles than are typical when it is administered alone. In yet another specific embodiment of the invention, a compound of this invention is administered for a greater number of cycles that would typically cause dose-limiting toxicity in a patient to whom a second active ingredient is not also being administered.

In one embodiment, a compound of this invention is administered daily and continuously for three or four weeks at a dose of from about 1 to about 5,000 mg/d followed by a break of one or two weeks. A compound of this invention is preferably administered daily and continuously at an initial dose of 1 to 5 mg/d with dose escalation (every week) by 10 to 100 mg/d to a maximum dose of 5,000 mg/d for as long as therapy is tolerated. In a particular embodiment, the compound is administered in an amount of about 400, 800, or 1,200 mg/day, preferably in an amount of about 800 mg/day for three to four weeks, followed by one week or two weeks of rest in a four or six week cycle.

In one embodiment of the invention, a compound of this invention and a second active ingredient are administered orally, with administration of a compound of this invention occurring 30 to 60 minutes prior to a second active ingredient, during a cycle of four to six weeks. In another embodiment of the invention, the combination of a compound of this invention and a second active ingredient is administered by intravenous infusion over about 90 minutes every cycle. In a specific embodiment, one cycle comprises the administration of from about 400 to about 800 mg/day of a compound of this invention and from about 50 to about 200 mg/m$^2$/day of a second active ingredient daily for 3 to 4 weeks and then one or two weeks of rest. In another specific embodiment, each cycle comprises the administration of from about 200 to about 400 mg/day of a compound of this invention and from about 50 to about 200 mg/m$^2$/day of a second active ingredient for three to four weeks followed by one or two weeks of rest. Typically, the number of cycles during which the combinatorial treatment is administered to a patient will be from about one to about 24 cycles, more typically from about two to about 16 cycles, and even more typically from about four to about eight cycles.

4.4 Pharmaceutical Compositions

Pharmaceutical compositions can be used in the preparation of individual, single unit dosage forms. Pharmaceutical compositions and dosage forms of the invention comprise a compound of this invention. Pharmaceutical compositions and dosage forms of the invention can further comprise one or more excipients.

Pharmaceutical compositions and dosage forms of the invention can also comprise one or more additional active ingredients. Consequently, pharmaceutical compositions and dosage forms of the invention comprise the active ingredients disclosed herein (e.g., a compound of this invention and optionally a second active agent). Examples of optional second, or additional, active ingredients are disclosed herein (see, e.g., section 4.2).

Single unit dosage forms of the invention are suitable for oral, mucosal (e.g. nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise a compound of this invention in an amount of from about 0.10 to about 150 mg. Typical dosage forms comprise a compound of this invention in an amount of about 0.1, 1, 2, 5, 7.5, 10, 12.5, 15, 17.5, 20, 25, 50, 100, 150 or 200 mg. In a specific embodiment, a preferred dosage form comprises a compound of this invention in an amount of about 5, 10, 25 or 50 mg. Typical dosage forms comprise the second active ingredient in an amount of 1 to about 1000 mg, from about 5 to about 500 mg, from about 10 to about 350 mg, or from about 50 to about 200 mg. Of course, the specific amount of the anti-cancer drug will depend on the specific agent used, the type of cancer being treated or managed, and the amount(s) of a compound of this invention and any optional additional active agents concurrently administered to the patient.

4.4.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their-ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W. R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises a compound of this invention, anhydrous lactose, microcrystalline cellulose, polyvinylpyrrolidone, stearic acid, colloidal anhydrous silica, and gelatin.

4.4.2 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.4.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention. For example, cyclodextrin and its derivatives can be used to increase the solubility of a compound of this invention. See, e.g., U.S. Pat. No. 5,134,127, which is incorporated herein by reference.

4.4.4 Topical and Mucosal Dosage Forms

Topical and mucosal dosage forms of the invention include, but are not limited to, sprays, aerosols, solutions, emulsions, suspensions, eye drops or other ophthalmic preparations, or other forms known to one of skill in the art. See, e.g., *Remington's Pharmaceutical Sciences*, $16^{th}$ and $18^{th}$ eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, $16^{th}$ and $18^{th}$ eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.4.5 Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a dosage form of a compound of this invention. Kits encompassed by this invention can further comprise additional active ingredients such as oblimersen (Genasense®), melphalan, G-CSF, GM-CSF, EPO, topotecan, dacarbazine, irinotecan, taxotere, WFN, COX-2 inhibitor, pentoxifylline, ciprofloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein (see, e.g., section 5.2).

Kits of the invention can further comprise devices that are used to administer the active ingredients. Examples of such devices include, but are not limited to, syringes, drip bags, patches, and inhalers.

Kits of the invention can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

Certain embodiments of the invention are illustrated by the following non-limiting examples.

5.1 2-(4-Amino-1-oxo-1,3-dihydro-isoindol-2-yl)-4-cabamoyl-butyric acid

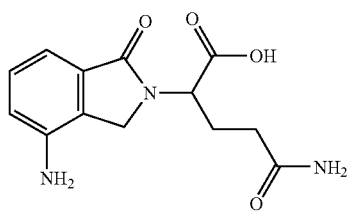

Step 1: To a suspension of methyl-2-bromomethyl-3-nitrobenzoate (10.6 g, 39 mmol) and L-glutamine t-butyl ester hydrochloride (9.2 g, 39 mmol) in THF (92 mL), was added TEA (12 mL) with stirring. The resulting mixture was refluxed for 12 hours and then cooled to ambient temperature. The mixture was concentrated to dryness, charged with water (100 mL) and MTBE (100 mL). The slurry was stirred at ambient temperature for 30 minutes. The solid was collected by vacuum filtration, washed with 0.2 N aqueous HCl (30 mL), DI water (30 mL×2), MTBE-(30 mL×3), and dried at 60° C. in vacuo overnight, giving 9.37 g (67% yield) of 4-carbamoyl-2-(4-notro-1-oxo-1,3-dihydro-isoindo-2-yl)-butyric acid t-butyl ester as a white powder. $^1$H NMR (DMSO-d$_6$): 8.48 (d, 1H), 8.17 (d, 1H), 7.84 (t, 1H), 7.24 (s, 1H), 6.78 (s, 1H), 4.94 (s, 2H), 4.75-4.81 (m, 1H), 2.10-2.33 (m, 4H), 1.41 (s, 9H).

Step 2: TFA (47 mL) was added to a stirred slurry of 4-cabamoyl-2-(4-nitro-1-oxo-1,3-dihydro-isoindo-2-yl)-butyric acid t-butylester (9.4 g, 26 mmol) in DCM (47 mL) at −15° C. over 55 minutes. The mixture was stirred at −15° C. for another 5 minutes after the addition of TFA. It was then allowed to warm to ambient temperature and stirring was continued at ambient temperature for an additional 5 hours. The reaction solution was concentrated in vacuo, stirred with 95 mL of ethyl acetate at ambient temperature for 16 hours. The solid was collected by vacuum filtration, washed with EtOAc (10 mL×2), and dried in vacuo at 60° C. for 15 hours, affording 7.60 g (95% yield) of a pale tan powder of 4-carbamoyl-2-(4-nitro-1-oxo-1,3-dihydro-isoindo-2-yl)-butyric acid. $^1$H NMR (DMSO-d$_6$): 13.14 (brs, 1H), 8.47 (d, 1H), 8.17 (d, 1H), 7.84 (t, 1H), 7.22 (s, 1H), 6.75 (s, 1H), 4.94 (s, 2H), 4.78-4.84 (m, 1H), 2.11-2.37 (m, 4H).

Step 3: 4-Carbamoyl-2-(4-nitro-1-oxo-1,3-isoindo-2-yl)-butyric acid (9.8 g, 32 mmol), 10% Pd/C (1 g), methanol (150 mL), and DI water (50 mL) were combined and shaken under 45-50 psi H$_2$ for 6 hours at ambient temperature. The reaction slurry was filtered through a celite bed and the celite bed was washed with 80 mL of methanol. The methanol wash and the filtrate were combined and concentrated in vacuo to dryness. The residue was then dissolved in DI water (200 mL), frozen in a dry-ice bath, and lyophilized for one week to provide 8.30 g of an off-white solid 2-(4-amino-1-oxo-1,3-dihydro-isoindol-2-yl)-4-carbamoyl-butyric acid in 90% yield: mp 158-160° C.; $^1$H NMR DMSO-d$_6$): 7.14-7.28 (m, 2H), 6.76-6.90 (m, 3H), 5.51 (brs, 2H), 4.71-4.77 (m, 1H), 4.16-4.32 (m, 2H), 1.90-2.32 (m, 4H) (showed 0.1 mol of MeOH and 0.4 mol H$_2$O); $^{13}$C NMR (DMSO-d$_6$): 173.19, 172.55, 169.06, 143.64, 132.41, 128.81, 125.74, 116.32, 110.44, 53.22, 48.65 (MeOH), 45.26, 31.60, 24.96. Analy. calculated for $C_{13}H_{13}N_3O_4$-0.4H$_2$O/0.1MeOH: 54.69% C, 5.68% H, 14.61% N, 2.5% H$_2$O. Found: 55.05% C, 5.42% H, 14.39% N, 3.6% H$_2$O.

5.2 4-(4-Amino-1-oxo-1,3-dihydro-isoindol-2-yl)-4-carbamoyl-butyric acid

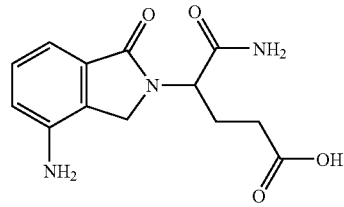

Step 1: To a suspension of methyl-2-bromomethyl-3-nitrobenxoate (5.8 g, 21 mmol) and L-isoglutamine t-butyl ester hydrochloride (5 g, 21 mmol) in THF (50 mL), was added TEA (6.5 mL) with stirring. The resulting mixture was refluxed for 24 hours and then cooled to ambient temperature. The mixture was concentrated to dryness, charged with water (75 mL) and MTBE (75 mL). The slurry was then stirred at ambient temperature for 2 hours. The solid was collected by vacuum filtration, washed with 0.2 N aqueous HCl (15 mL), DI water (20 mL×7 to neutral pH), and MTBE (20 mL). The wet cake was further reslurried at ambient temperature for 16.5 hours in a mixture of solvent containing MTBE (100 mL) and DI water (50 mL). The solid was collected by vacuum filtration, washed with MTBE (65 mL), and dried at 60° C. in vacuo for 15 hours, giving 5.30 g (70% yield) of 4-carbamoyl-4-(4-nitro-1-oxo-1,3-dihydro-isoindo-2-yl)-butyric acid t-butyl ester as a pale tan powder. mp 174-176° C.; $^1$H NMR (DMSO-d$_6$): 8.45 (d, 1H), 8.16 (d, 1H), 7.82 (t, 1H), 7.64 (s, 1H), 7.27 (s, 1H), 4.98 (dd, 2H), 4.78 (dd, 1H), 2.00-2.25 (m, 4H), 1.33 (s, 9H); $^{13}$C NMR (DMSO-d$_6$): 171.49, 171.37, 165.81, 143.27, 137.80, 135.00, 129.91, 129.56, 126.73, 79.80, 53.75, 48.17, 31.65, 27.65, 24.83 ppm. Analy. calculated for $C_{17}H_{31}N_3O_6$: 56.19% C, 5.83% H, 11.56% N. Found: 55.89% C, 5.53% H, 11.26% N.

Step 2: TFA (26 mL) was added to a stirred slurry of 4-carbamoyl-4-(4-nitro-1-oxo-1,3-dihydro-isoindo-2-yl)-butyric acid t-butyl ester (5.2 g, 14 mmol) in DCM (26 mL) at −15° C. over 25 minutes. The mixture was stirred at −15° C. for another 5 minutes after the addition of TFA. It was then allowed to warm to ambient temperature and stirring was continued at ambient temperature for an additional 4 hours. The reaction solution was concentrated in vacuo, stirred with 52 mL of ethyl acetate at ambient temperature for 15 hours. The solid was collected by vacuum filtration, washed with EtOAc twice (14+21 mL), and reslurried in acetone (20 mL) at ambient temperature for 2 hours. The suspension was filtered and the solid was washed with acetone (27 mL×2). The solid was dried in vacuo at 60° C. for 2 hours, affording 4.17 g (95% yield) of 4-carbamoyl-4-(4-nitro-1-oxo-1,3-dihydro-isoindo-2-yl)-butyric acid as a pale tan powder. mp 219-221° C.; $^1$H NMR (DMSO-$d_6$): 12.14 (brs, 1H), 8.46 (d, 1H), 8.16 (d, 1H), 7.82 (t, 1H), 7.67 (s, 1H), 7.29 (s, 1H), 5.00 (dd, 2H), 4.77-4.82 (m, 1H), 1.99-2.26 (m, 4H); $^{13}$C NMR (DMSO-$d_6$): 173.63, 171.65, 165.89, 143.31, 137.85, 135.00, 129.92, 129.59, 126.76, 53.78, 48.19, 30.58, 24.97. Analy. calculated for $C_{13}H_{13}N_3O_6 \cdot 0.2H_2O$: 50.23% C, 4.34% H, 13.52% N, 1.2% $H_2O$. Found: 50.23% C, 4.06% H, 13.23% N, 1.2% $H_2O$.

Step 3: 4-Carbamoyl-4-(4-nitro-1-oxo-1,3-dihydro-isoindo-2-yl)-butyric acid (8.8 g, 29 mmol), 10% Pd/C (0.88 g), methanol (132 mL), and DI water (44 mL) were combined and shaken under 45-50 psi $H_2$ for 6 hours at ambient temperature. The reaction slurry was filtered through a celite bed and the celite bed was washed with 75 mL of methanol. The methanol wash and the filtrate were combined and concentrated in vacuo to dryness. DI water (100 mL) was added to the residue, and the mixture was again concentrated to dryness. The residual oily material was then dissolved in DI water (200 mL), frozen in a dry-ice bath, and lyophilized for 8 days to provide 7.30 g of 4-(4-amino-1-oxo-1,3-dihydro-isoindol-2-yl)-4-carbamoyl-butyric acid as an off-white solid in 92% yield. mp 334-336° C.; $^1$H NMR (DMSO-$d_6$): 12.07 (brs, 1H), 7.54 (s, 1H), 6.76-7.20 (m, 4H), 5.42 (brs, 2H), 4.71-4.75 (m, 1H), 4.32 (dd, 2H), 1.90-2.22 (m, 4H); $^{13}$C NMR (DMSO-$d_6$): 173.62, 172.16, 168.84, 143.39, 132.48, 128.68, 126.06, 116.28, 110.53, 53.26, 45.31, 30.69, 25.09. Analy. calculated for $C_{13}H_{15}N_3O_4 \cdot 0.2H_2O$: 55.59% C, 5.53% H, 14.96% N, 1.3% $H_2O$. Found: 55.69% C, 5.30% H, 14.83% N, 1.4% $H_2O$.

5.3 4-Carbamoyl-4-[4-[(furan-2-yl-methyl)-amino]-1,3-dioxo-1,3-dihydro-isoindol-2-yl]-butyric acid

5.3.1 3-[(Furan-2-ylmethyl)-amino]-phthalic acid dimethyl ester

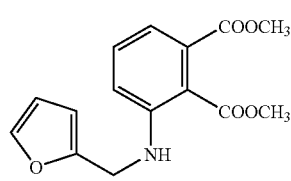

To a stirred solution of 3-amino-phthalic acid dimethyl ester (8.23 g, 39.32 mmol) in methylene chloride (200 ml) under a nitrogen atmosphere, 2-furaldehyde (8.14 ml, 98.30 mmol) and acetic acid (13.57 ml, 235.92 mmol) were added. The mixture was stirred for 5 minutes, followed by addition of sodium triacetoxyborohydride (25 g, 117.96 mmol). The reaction was stirred overnight, washed with water (2×200 ml), saturated aqueous sodium bicarbonate (2×200 ml), and brine (200 ml), and dried over $MgSO_4$. The solvent was evaporated in vacuo to give a brown oil (12.42 g), which was used directly without purification.

5.3.2 3-[(Furan-2-yl-methyl)-amino]-phtalic acid

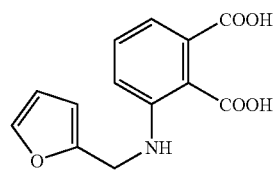

To a stirred solution of crude 3-[(furan-2-yl-methyl)-amino]-phthalic acid dimethyl ester in methanol (100 ml), was added 5N potassium hydroxide (79 ml). The mixture was stirred at room temperature overnight. The solvent was evaporated in vacuo and the residue dissolved in water (50 ml). The water was washed with diethyl ether (2×100 ml). The aqueous portion was cooled in an ice bath and the pH was adjusted to 2-3 by dropwise addition of concentrated hydrochloric acid. The aqueous solution was then extracted into ethyl acetate (3×100 ml). The combined ethyl acetate extracts were washed with brine (150 ml), and dried over $MgSO_4$. The solvent was evaporated in vacuo, and the residue, which contained a mixture of diacid and monomethyl esters, was used without further purification.

5.3.3 4-Carbamoyl-4-{4-[(furan-2-yl-methylamino]-1,3-dioxo 1,3-dihydro-isoindol-2-yl}-butyric acid

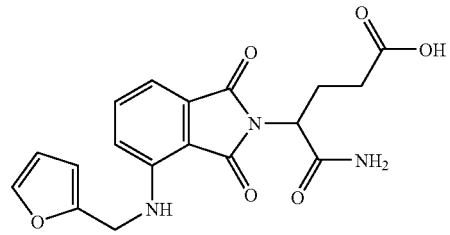

To a stirred solution of 3-[(furan-2-yl-,ethyl)-amino]-phthalic acid (0.5 g, 1.93 mmol) in pyridine (20 ml), was added 4-amino-4-carbamoyl-butyric acid (0.31 g, 2.12 mmol). The reaction mixture was heated to reflux overnight. The solvent was evaporated in vacuo. The resulting residue was dissolved in saturated sodium bicarbonate (50 ml) and washed with ethyl acetate (2×50 ml). The aqueous portion was cooled in an ice bath, and the pH was adjusted to 2-3 by dropwise addition of concentrated hydrochloric acid. The aqueous solution was then extracted into ethyl acetate (3×50 ml). The combined ethyl acetate extracts were washed with brine (100 ml), and dried over $MgSO_4$. The solvent was evaporated in vacuo to give an oil. The oil was purified by flash column chromatography (60% ethyl acetate/39% hexane/1% formic acid) to give an oil, which was triturated in diethyl ether (30 ml). The resulting yellow solid was filtered and dried (0.14 g, 20%): mp 120-122° C.; $^1$H NMR (DMSO-d$_6$) δ 12.09 (s, 1H), 7.59-7.62 (m, 3H), 7.15 (d, J=8.25 Hz, 2H), 7.03-6.93 (m, 2H), 6.41-6.36 (m, 2H), 4.56-4.50 (m, 3H), 2.40-2.17 (m, 4H); $^{13}$C NMR (DMSO-d$_6$) δ 173.57, 170.04, 169.36, 167.71, 152.07, 145.57, 142.41, 135.60, 132.55, 116.99, 110.70, 110.46, 110.42, 107.41, 51.73, 30.66, 23.52; Analy. Calculated for C$_{18}$H$_{17}$N$_3$O$_6$: C, 57.25; H, 4.72; N, 11.13 (+0.35H$_2$O). Found: C, 57.50; H, 4.59; N, 10.93.

5.4 4-Carbamoyl-2-{4-[(furan-2-yl-methyl)-amino]-1,3-dioxo-1,3-dihydro-isoindol-2-yl}-butyric acid

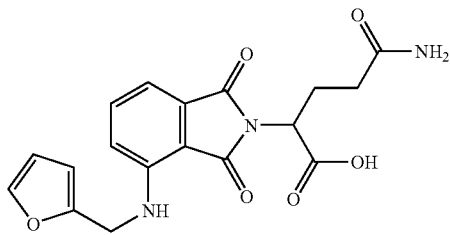

2-Amino-4-carbamoyl-butyric acid (0.31 g, 2.11 mmol) was treated using the procedures substantially the same as those described in Section 5.3, above, for the synthesis of 4-carbamoyl-2-{4-[(furan-2-yl-methyl)-amino]-1,3-dioxo-1,3-dihydro-isoindol-2-yl}-butyric acid. The residue was purified by flash column chromatography (66% ethyl acetate/33% hexane/1% formic acid) to give an oil (0.44 g). Further purification by preparative reverse phase HPLC (38% acetonitrile/62% water, isocratic) provided an oil, which was triturated in diethyl ether (30 ml). The resulting yellow solid was filtered and dried (0.31 g, 44%): mp 114-116° C.; $^1$H NMR (DMSO-d$_6$) δ 13.14 (s, 1H), 7.59-7.54 (m, 2H), 7.19-7.16 (m, 2H), 7.05-6.97 (m, 2H), 6.70 (s, 1H), 6.41-6.36 (m, 2H), 4.64 (dd, J=4.49 Hz and J=10.49 Hz, 1H), 4.55 (d, J=6.01 Hz, 2H), 2.42-2.17 (m, 2H), 2.14-2.02 (m, 2H); $^{13}$C NMR (DMSO-d$_6$) δ 173.03, 170.61, 169.06, 167.48, 151.99, 145.72, 142.44, 135.94, 132.13, 117.39, 110.89, 110.43, 109.79, 107.43, 50.93, 31.35, 24.02, 15.14; Analy. Calculated for C$_{19}$H$_{17}$N$_3$O$_6$: C, 57.38; H, 4.71; N, 11.15 (+0.30H$_2$O). Found: C, 57.00; H, 4.85; N 10.83.

5.5 2-{4-[(Furan-2-yl-methyl)-amino]-1,3-dioxo-1,3-dihydro-isoindol-2-yl}4-phenylcarbamoyl-butyric acid

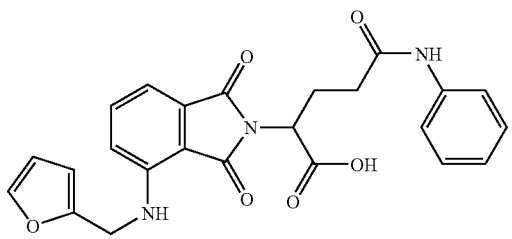

2-Amino-4-phenylcarbamoyl-butyric acid (0.49 g, 2.20 mmol) was treated according to the procedures substantially the same as those described in Section 5.3, above, for the synthesis of 2-{4-[(furan-2-yl-methyl)-amino]-1,3-dioxo-1,3-dihydro-isoindol-2-yl}-4-phenylcarbamoyl-butyric acid. The residue was purified by flash column chromatography (45% ethyl acetate/54% hexane/1% formic acid) to provide a yellow solid (0.48 g, 53.6%): mp 146-148° C.; $^1$H NMR (DMSO-d$_6$) δ 13.13 (s, 1H), 9.81 (s, 1H), 7.59-7.38 (m, 4H), 7.26-7.14 (m, 3H), 7.04-6.96 (m, 3H), 6.40-6.34 (m, 2H), 4.71 (dd, J=3.80 Hz and J=9.50 Hz, 1H), 4.54 (d, J=5.95 Hz, 2H), 2.46-2.22 (m, 4H); $^{13}$C NMR (DMSO-d$_6$) δ 170.51, 169.95, 169.05, 167.46, 151.99, 145.73, 142.42, 139.07, 135.93, 132.12, 128.50, 122.88, 119.01, 117.39, 110.91, 110.43, 109.80, 107.39, 50.78, 32.75, 23.97; Analy. Calculated for C$_{24}$H$_{21}$N$_3$O$_6$: C, 63.63; H, 4.81; N, 9.28 (+0.31H$_2$O). Found: C, 63.38; H, 4.84; N, 9.20.

5.6 2-[4-[(Furan-2-yl-methyl)-amino]-1,3-dioxo-1,3-dihydro-isoindol-2-yl]-pentanedioic acid

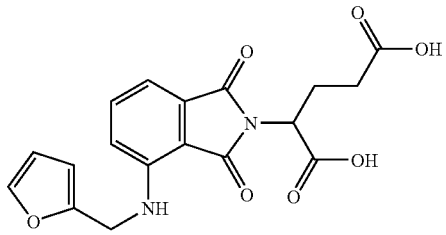

2-Amino-pentanedioic acid (0.32 g, 2.18 mmol) was treated using procedures substantially the same as those described in Section 5.3, above, for the synthesis of 2-{4-[(furan-2-yl-methyl)-amino]-1,3-dioxo-1,3-dihydro-isoindol-2-yl}-pentanedioic acid. The residue was purified by flash column chromatography (42.5% ethyl acetate/56.5% hexane/1% formic acid) to provide a yellow solid (0.54 g, 73%): mp 150-152° C.; $^1$H NMR (DMSO-d$_6$) δ 12.62 (s, 2H), 9.81 (s, 1H), 7.60-7.54 (m, 2H), 7.17 (d, J=8.58 Hz, 1H), 7.05-6.98 (m, 2H), 6.41-6.36 (m, 2H), 4.72 (dd, J=4.10 Hz and J=9.80 Hz, 1H), 4.56 (d, J=6.05 Hz, 2H), 2.38-2.20 (m, 4H); $^{13}$C NMR (DMSO-d$_6$) δ 173.59, 170.47, 169.04, 167.46, 151.98, 145.74, 142.42, 135.94, 132.10, 117.42, 110.93, 110.42, 109.77, 107.40, 95.55, 50.55, 30.29, 23.69; Analy. Calculated for C$_{18}$H$_{16}$N$_2$O$_7$: C, 57.40; H, 4.40; N, 7.40 (+0.17H$_2$O+0.02 EtOAc+0.02 CH$_2$Cl$_2$). Found: C, 57.01; H, 4.18; N, 7.27.

5.7 Cyclopropanecarboxylic acid {2-[1-(3-ethoxy-4-methoxy-phenyl)-2-[1,3,4]oxadiazol-2-yl-ethyl]-3-oxo-2,3-dihydro-1H-isoindol-4-yl}-amide

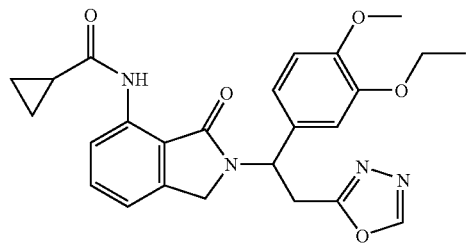

Cyclopropanecarboxylic acid {2-[1-(3-ethoxy-4-methoxy-phenyl)-2-[1,3,4]oxadiazol-2-yl-ethyl]-3-oxo-2,3-dihydro-1H-isoindol-4-yl}-amide was prepared by reacting 3-[7-

(cyclopropanecarbonyl-amino)-1-oxo-1,3-dihydro-isoindol-2-yl]-3-(3-ethoxy-4-methoxy-phenyl)-propionic acid (400 mg, 0.9 mmol), CDI (160 mg, 1.0 mmol) and formic hydrazide (0.09 g, 1.5 mmol) in THF (5 mL). The crude was then reacted with phosphorus oxychloride (0.18 mL, 1.9 mmol) in acetonitrile (15 mL). The product was obtained as a white solid (60 mg, 15% yield): mp 181-183° C.; $^1$H NMR (CDCl$_3$) δ 0.86-0.92 (m, 2H, cyclopropyl CH$_2$), 1.06-1.11 (m, 2H, cyclopropyl CH$_2$), 1.45 (t, J=7.5 Hz, 3H, CH$_3$), 1.58-1.68 (m, 1H, cyclopropyl CH), 3.66 (dd, J=5, 15 Hz, 1H, CHH), 3.85 (dd, J=10, 15 Hz, 1H, CHH), 3.87 (s, 3H, CH$_3$), 4.03-4.11 (m, 3H, OCH$_2$CH$_3$+CHH), 4.43 (d, J=17 Hz, 1H, CHH), 5.86-5.91 (m, 1H, NCH), 6.85-6.90 (m, 2H, Ar), 6.96-7.01 (m, 2H, Ar), 7.43 (t, J=7.5 Hz, 1H, Ar), 8.35 (s, 1H, Ar), 8.41 (d, J=7.5 Hz, 1H, Ar), 10.41 (s, 1H, NH); $^{13}$C NMR (CDCl$_3$), 8.27, 8.29, 14.73, 16.16, 28.04, 46.36, 52.26, 55.98, 64.64, 111.53, 112.36, 116.80, 116.96, 117.80, 119.16, 129.54, 133.43, 138.06, 141.25, 148.84, 149.64, 153.34, 163.79, 169.50, 172.66. Analy. calculated for C$_{25}$H$_{25}$N$_4$O$_5$+ 0.1H$_2$O: C, 64.47; H, 5.69; N, 12.07. Found: C, 64.50; H, 5.70; N, 11.69.

5.8 Inhibition of MM Cell Proliferation

The ability of a compound of this invention to effect the proliferation of multiple myeloma (MM) cell lines is investigated in an in vitro study. Uptake [$^3$H]-thymidine by different MM cell lines (MM. IS, Hs Sultan, U266 and RPMI-8226) is measured as an indicator of cell proliferation. Cells are incubated in the presence of compound for 48 hours; [$^3$H]-thymidine is included for the last 8 hours of the incubation period.

5.9 In Vivo LPS-Induced TNF-α Production Assay

Male CD rats procured from Charles River Laboratories at seven weeks of age are allowed to acclimate for one week prior to use. A lateral tail vein is cannulated percutaneously with a 22-gage over-the-needle catheter under brief isoflurane anesthesia. Rats are administered a compound of this invention either by intravenous injection via the tail vein catheter or oral gavage 15 to 180 min prior to injection of 0.05 mg/kg LPS (*E. Coli* 055:B5). Catheters are flushed with 2.5 mL/kg of normal injectable saline. Blood is collected via cardiac puncture 90 minutes after LPS challenge. Plasma is prepared using lithium heparin separation tubes and frozen at −80° C. until analyzed. TNF-α levels are determined using a rat specific TNF-α ELISA kit (Busywork). The ED$_{50}$ values are calculated as the dose of the compound of this invention at which the TNF-α production is reduced to 50% of the control value.

5.10 Cycling Therapy in Patients

In a specific embodiment, a compound of this invention are cyclically administered to patients with cancer. Cycling therapy involves the administration of a first agent for a period of time, followed by a rest for a period of time and repeating this sequential administration. Cycling therapy can reduce the development of resistance to one or more of the therapies, avoid or reduce the side effects of one of the therapies, and/or improves the efficacy of the treatment.

In a specific embodiment, prophylactic or therapeutic agents are administered in a cycle of about four to six weeks, about once or twice every day. One cycle can comprise the administration of a therapeutic on prophylactic agent for three to four weeks and at least one week or two weeks of rest. The number of cycles administered is from about one to about 24 cycles, more typically from about two to about 16 cycles, and more typically from about four to about eight cycles.

5.11 Clinical Studies in Patients with Relapsed Multiple Myeloma

Patients with relapsed and refractory Dune-Salmon stage III multiple myeloma, who have either failed at least three previous regimens or presented with poor performance status, neutropenia or thrombocytopenia, are treated with up to four cycles of combination melphalan (50 mg intravenously), a compound of this invention (about 1 to 5,000 mg orally daily), and dexamethasone (40 mg/day orally on days 1 to 4) every four to six weeks. Maintenance treatment consisting of daily a compound of this invention and monthly dexamethasone are continued until the disease progression. The therapy comprising the administration of a compound of this invention in combination with melphalan and dexamethasone is highly active and generally tolerated in heavily pretreated multiple myeloma patients whose prognosis is otherwise poor.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

All of the patents, patent publications and references cited herein are incorporated in their entirety by reference. However, citation of such references do not constitute an admission that such references are prior art. This invention can be better illustrated by the following claims.

What is claimed is:

1. A compound of formula:

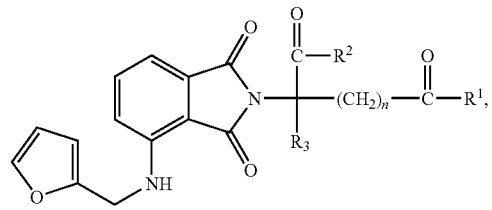

or a pharmaceutically acceptable salt or stereoisomer thereof, wherein
   R$^1$ and R$^2$, independently of the other, is hydroxyl or NH—Z;
   R$^3$ is hydrogen;
   Z is hydrogen or aryl; and
   n is 0, 1 or 2.

2. A pharmaceutical composition comprising a compound of claim 1.

* * * * *